US006418339B1

(12) United States Patent
Essenpreis et al.

(10) Patent No.: US 6,418,339 B1
(45) Date of Patent: Jul. 9, 2002

(54) METHOD AND APPARATUS FOR DETERMINING THE LINES OF OPTIMAL DIRECTION FOR SURGICAL CUTS IN THE HUMAN SKIN

(76) Inventors: Matthias Essenpreis, 38775 Stonington Ter., Fremont, CA (US) 94536; Stephen Nickell, Implerstr. 53, 81371 Munich (DE); Dirk Bocker, 1652 Castillej Ave., Palo Alto, CA (US) 94306

(*) Notice: Subject to any disclaimer, the term of this patent is extended or adjusted under 35 U.S.C. 154(b) by 0 days.

(21) Appl. No.: 09/424,086
(22) PCT Filed: Apr. 18, 1998
(86) PCT No.: PCT/DE98/01090
§ 371 (c)(1),
(2), (4) Date: Nov. 16, 1999
(87) PCT Pub. No.: WO98/53739
PCT Pub. Date: Dec. 3, 1998

(30) Foreign Application Priority Data

May 26, 1997 (DE) .......................................... 197 21 902

(51) Int. Cl.[7] .................................................. A61B 6/00
(52) U.S. Cl. ........................ 600/476; 356/342; 128/898
(58) Field of Search ................................. 600/476, 473, 600/407; 356/340, 342; 606/2, 9, 10, 13

(56) References Cited

U.S. PATENT DOCUMENTS

| 5,825,488 A | * | 10/1998 | Kohl et al. ................. 356/342 |
| 5,851,181 A | * | 12/1998 | Talmor ........................ 600/476 |
| 5,853,370 A | * | 12/1998 | Chance et al. ............... 600/473 |
| 5,986,770 A | * | 11/1999 | Hein et al. ................... 600/476 |
| 6,032,071 A | * | 2/2000 | Binder ......................... 600/476 |
| 6,045,511 A | * | 4/2000 | Ott et al. ...................... 600/504 |
| 6,055,451 A | * | 4/2000 | Bambot et al. .............. 600/476 |
| 6,070,092 A | * | 5/2000 | Kazama et al. ............. 600/310 |
| 6,205,353 B1 | * | 3/2001 | Alfano et al. ................ 600/476 |
| 6,216,540 B1 | * | 4/2001 | Nelson et al. ................. 73/633 |

* cited by examiner

*Primary Examiner*—Marvin M. Lateef
*Assistant Examiner*—Shawna J Shaw
(74) *Attorney, Agent, or Firm*—Daniel L. Dawes; Myers, Dawes & Andras LLP

(57) ABSTRACT

The invention relates to a method and a device for in vivo detection of the direction of Langer's lines in the skin. Light is irradiated into the skin as primary light at one defined site (7) identified through the epidermis (6) in such a way that it is transported in the skin (5) by scattering or absorption, while part of said irradiated light emerges from the skin as secondary light in the region surrounding the irradiated site. An amplitude-dependent property of secondary light emerging from the skin (5) around the irradiated site is measured in order to determine the preferential direction of the diffuse light transport in the skin (5) and, consequently, determine the orientation of Langer's lines thereof.

17 Claims, 4 Drawing Sheets

METHOD AND APPARATUS FOR DETERMINING THE LINES OF OPTIMAL DIRECTION FOR SURGICAL CUTS IN THE HUMAN SKIN

RELATED APPLICATIONS

The present application is a national phase PCT patent application under 35 USC 371 of serial no. PCT/DE98/01090 filed on Apr. 18, 1998 claiming priority from German application serial no. 197 21 902.0 filed on May 26, 1997.

BACKGROUND OF THE INVENTION

1. Field of the Invention

The invention relates to a method and a device for in vivo detection of the direction of Langer's lines in the skin.

2. Description of the Prior Art

Langer's lines (*Sulci cutis*) define the direction within the human skin along which the skin is least flexible. This mechanical property is determined by the alignment of collagen fibers and bundles of collagen fibers within the dermis.

The fundamental research on this property of the human skin was carried out by K. Langer and was already published in 1861. To determine the direction of the Langer's lines, he multiply pierced human cadaver skin at short distances. Although his piercing instrument was of circular shape, the resulting holes were of ellipsoidal shape. Langer observed patterns of the directions of the longer axes of the ellipsoidal holes on a skin area. Subsequently, these patterns were given the name "Langer's lines" according to it's discoverer.

The knowledge of the direction of Langer's lines within a particular area of the skin is of great importance for surgical operations. Generally and most importantly, a surgical cut should allow for an optimal opening of the area to be operated on and should also offer the possibility to extend the area during the surgery. At the same time, it must be made sure that the skin can heal properly after the surgery and that a beneficial cosmetic appearance is obtained after healing. These conditions are usually best fulfilled, if a surgical cut is carried out in the direction of Langer's lines. The generation of scares, in particular, is minimized under these conditions. This is of paramount importance in plastic surgery, where surgical cuts and potential scars run through visible body parts, such as the face.

Unfortunately, the accurate direction of Langer's lines often is not known. In some areas of the body, large differences exist in the direction between different persons. Even on the same person, changes in the exact direction may occur during the course of life. To account for these variations in the direction of Langer's lines during surgery, it is necessary to determine the direction using a non invasive method. With such a method, even less experienced surgeons would be enabled to plan a surgical cut with minimal scaring. This could reduce the esthetic and psychological problems associated with large scars and eliminate the need for post-operative treatment of scaring.

Despite the large importance of this problem, a suitable method for non-invasive measurement of Langer's lines is not yet available. In the past it was attempted to use mechanical tension measurements on the skin surface as e.g. described by J. C. Barbenell in an article "Identification of Langer's Lines", pp. 341–344 in: Handbook of Non-Invasive Methods and the Skin, CRC Press, Boca Raton, 1995. In this publication, it becomes obvious that the described mechanical method does not give reliable information about the direction of Langer's lines in the skin.

BRIEF SUMMARY OF THE INVENTION

The goal of the invention is to measure the direction and the pattern of directions of Langer's lines on the skin surface non invasively and painlessly.

This problem is solved using light penetrating the skin. Light is irradiated as primary light into the skin at a defined site on the skin surface, in such a way that the light is transported in the skin by scattering and absorption. Part of said irradiated light emerges from the skin as secondary light in the region surrounding the irradiation site. As a measure of the direction of Langer's lines, the dependence of a measurable property of the secondary light is measured as a function of the polar angle around the irradiation site and the preferential direction of light transport in the skin is determined. This preferential direction of light transport indicates the direction of Langer's lines.

A measurable property of the light (subsequently also termed "measurement parameter") is, particularly, the intensity of light. Other measurable properties of the light can also be used to determine the preferential direction of the diffuse light transport in the skin. E.g. the intensity of the primary light can be modulated. In this case, the AC amplitude (modulation) of the measured secondary light can be used to obtain information about the preferential direction of the diffuse light transport. When polarized light is used as primary light, the degree of polarization of the secondary light may be used. Generally, any measurable property of the secondary light, which contains information about the preferential direction of the diffuse light transport in the skin can be used. Subsequently, it is referred to the intensity as the measurement parameter as an example without restricting the use to using the intensity as the measurement parameter.

To determine the polar angle dependence, the primary light is irradiated into the skin within a small, specially confined area (irradiation site). A requirement for the determination of the polar angle dependence around the irradiated area is the measurement of the intensity of the secondary light on at least two detection sites. The polar angle (with respect to the irradiation area) of the at least two detection sites must have an orthogonal component. If only two detection sites are used, a difference in the polar angle of 90° is preferred, whereas the difference in the polar angle should be at least 35°.

At least three detection sites should be used to achieve an adequate resolution of the measured polar angle dependence of the measurable property. The difference in polar angle of the measurement locations should preferably be smaller than 20°. Especially preferred is the measurement of the measurement parameter at a multitude of locations located around the irradiated area, for which an angular resolution of at least 20° is preferred, i.e. the difference in polar angle between two neighboring measurement locations is not larger than 20°.

The wavelength of the primary light is preferably between 400 nm and 1400 nm. It is furthermore preferred, with respect to the accuracy of the measurement, that the light is predominantly monochromatic. It is sufficient, if the maximum half width is smaller than 200 nm, preferably smaller than 100 nm. Furthermore, the accurate determination of the preferential direction of light transport and therefore the determination of the direction of Langer's lines may be improved by using polarized light as primary light. Under certain conditions it may also be helpful to place a polarization filter between detection area and light detector.

Different detection sites can be obtained by using flexible detection means, e.g. light guiding fibers, which are moved from detection site to detection site. Especially preferred are embodiments, which incorporate a multitude of detection means to measure the polar angle dependence. In this embodiment, the individual detection means are positioned in a fixed location with respect to the irradiation site and measure the intensity of the secondary light with emerges from the skin at a defined detection site.

The detection sites, of which the measurement parameters are used to determine a polar angle dependence around the irradiated site, are preferably aligned on a circle around the irradiated site to ensure equal distances to the irradiated site. This eases the subsequent mathematical manipulation of the data. Furthermore, it was observed that the anisotropy for different distances between irradiation site and detection areas varies with the location of the human body. The reason for this effect is the dependence of the penetration depth of the light on the distance between irradiation area and detection area.

The measurement of the polar dependence of light intensity can generally be achieved with methods and means, which are known for other purposes, however, special requirements of the measurement need to be accounted for. WO 94/101 describes a method for measurement of glucose in skin, for which the analytical result is determined from a number of spacially dependent light scattering measurements. For these measurements, light is irradiated into the skin at a defined site on the skin (irradiated site) and the light intensity measured from a second defined site on the skin in the surrounding area (detection area) of the irradiated site. A special, chess board like alignment of irradiating light sources (especially light emitting diodes) and light detectors (especially photo diodes) can be used in particular for this purpose. A very suitable apparatus for such measurements and other measurements of light transport in the skin is described in the European Patent with the publication number 0777119. This apparatus uses an optical fiber plate (face plate) which is in contact with the skin and facilitates the transmission of light from the detection sites on the surface of the skin to the light detectors in the apparatus. In addition to the descriptions in this invention it is referred to these publications.

It is assumed in these references that the light transport in the skin, as governed by optical absorption and scattering, generally is isotropic in the skin surrounding a spacially limited irradiated site. Disturbances of the isotropic light diffusion are only expected to come from special heterogeneous structures in the skin, such as pigmented areas or blood vessels close to the skin surface.

A number of publications describe the detection of structures, particularly tumors, below the skin surface using light penetrating the skin. This is discussed e.g. in WO 96/04545 and the corresponding references. Again, in this publication it is assumed that the light transport in the skin is generally isotropic, apart from the heterogeneous structures the method wants to detect.

In contrast to the assumption of these referenced publications, it has been discovered that the light transport in the skin is surprisingly and significantly anisotropic when the special measurement situation is used as disclosed in this invention. Furthermore, it has been discovered that the direction of anisotropy of the light transport indicates the direction of Langer's lines.

The invention will be explained in more detail below by means of the figures.

DETAILED DESCRIPTION OF THE PREFERRED EMBODIMENTS

The device for detection of Langer's Lines shown in FIGS. 1 to 4, has the form of a thick pencil to enable an easy and precise use. It consists of an upper component [2] which has a cylindrical shape and a skin contact component [3], the bottom surface area of which is brought in direct contact with the skin [5] and is therefore called the skin contact area [4].

A light source [8], preferably consisting of a light emitting diode (LED) or laser diode (LD), is used to transmit primary light through the skin surface [6] into the skin [5]. The light transmission area [9] at which the primary light passes through the contact area [4] is located in the center of the contact area [4]. The form and size of the light transmission area [7] is that of a point irradiation on the surface [6] of the skin [5]. The diameter of the light transmission zone is preferably smaller than 1 mm, especially preferred is a diameter smaller than 0.5 mm. The preferred embodiment shows an optical connection between light source [8] and light transmission zone [9] using a light guide [10]. The elements, which are used to transmit the light into the skin at an irradiated site (in the displayed embodiment a light source [8] and light guide [10]), are called illumination means [11].

Detection means [14] are used to measure the polar angle dependence of the intensity of light emerging from the skin [5] near the light irradiation site [7]. Each of the detection means [14] is designed such that the intensity of the emerging light is measured at a defined detection site [15] which forms (as in the case of the irradiation site [7]) a defined, spacially limited area on the skin surface [6].

Figure 4:
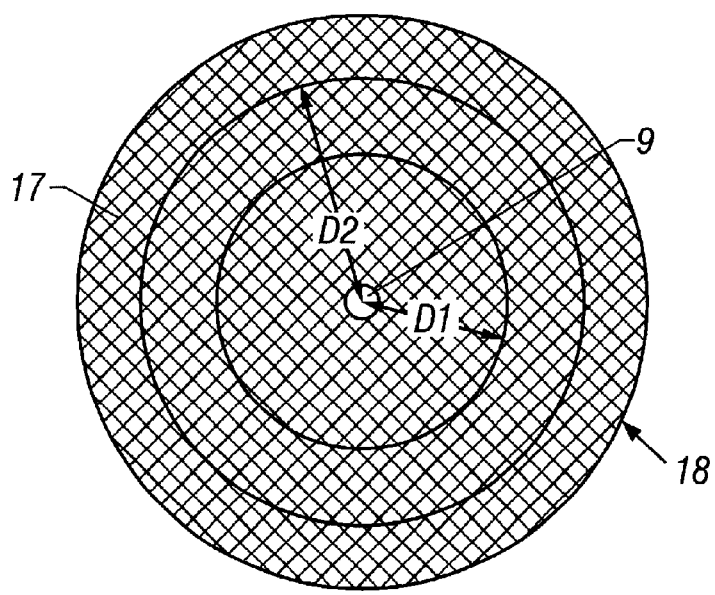
FIG. 4 shows a surface view of the light detection unit along the line IV–V as shown in FIG. 3.

As shown, the preferred embodiment uses a number of detection means [14], which allow the measurement of light intensity at a number of detection sites [15]. The detectors [17] (light sensitive elements) of the detection means [14] are formed on a semiconductor surface [16], which has light sensitive areas at the respective locations. A regular alignment of the detectors [17] is preferred. Such a component can be obtained commercially in form of a CCD array [18], especially in form of arrays for video cameras. FIG. 4 symbolically shows the regular alignment of the light sensitive areas [17] of such a CCD array.

Within the preferred embodiment, the optical connection between detectors [17] and the corresponding light transmission area of the secondary light [21] within the contact area [4] is realized in form of an optical fiber plate [20]. The fiber plate consists of a large number of densely packed optical fibers, which are aligned orthogonally to the contact area [4]. Such optical fiber plates are commercially available. The thickness (equivalent to the length of the fibers) is preferably less than 5 mm. A thickness between 1 and 2 mm has been shown to be particularly suitable. Further details can be found in EP-A 0777119.

The diameter of optical fibers of suitable optical fiber plates is very small to ensure the optical connection between a detector [17] and a corresponding light transmission area [21] be made by a large number of optical fibers. The lines in FIG. 3, which run in vertical direction to the contact area [4] through the optical fiber plate [20] do not indicate individual fibers, but the light transmission areas for the secondary light [21], corresponding to the individual detectors [17]. Because of a very small light transmission between fibers within the fiber plate (cross talk), the dimensions of the light transmission areas [21] (and therefore the dimensions of the corresponding detection sites [15]) are given by the dimensions of the light sensitive areas of the detectors [17]. Additionally, a mask can be used on at least one side of the fiber plate [20] to define the dimensions of the light detection sites [21], as described in EP-A-07771119.

Preferably, the detectors [17] are rigidly and stationarily (especially by adhesive fixation or equivalent permanent fixation) connected to the detector side [23] of the fiber plate [20]. Especially preferred is the shown embodiment, in which the detectors [17] are aligned on a common semiconductor substrate [18]. This embodiment enables a compact construction with a high mechanical stability, which supports the optical stability.

The detectors [17] generate electrical measurement signals, which correspond to the light intensity on the light sensitive areas. The electrical signals are transmitted to an electronic unit [25]. This unit contains electronic means to control the light source [8] and to derive the information about the polar angle dependence of the secondary light, which is emitted from the skin [5] from the measurement signals generated by the detectors [17]. Furthermore, the electronic unit [25] contains electronic means to control the display means, which are used to display the preferential direction (Langer's Lines) of light transport with respect to the skin surface and which are discussed below. The electronic unit [25] can therefore described as data processing and control unit.

There is an electrical power source [26], suitably a (rechargeable) battery. The electrical leads, which connect the electronic unit [25] to the detection and display means, are only shown as single connections despite the fact that, naturally, a number of leads, equivalent to the number of signals to be transmitted, are used.

Figure 8:
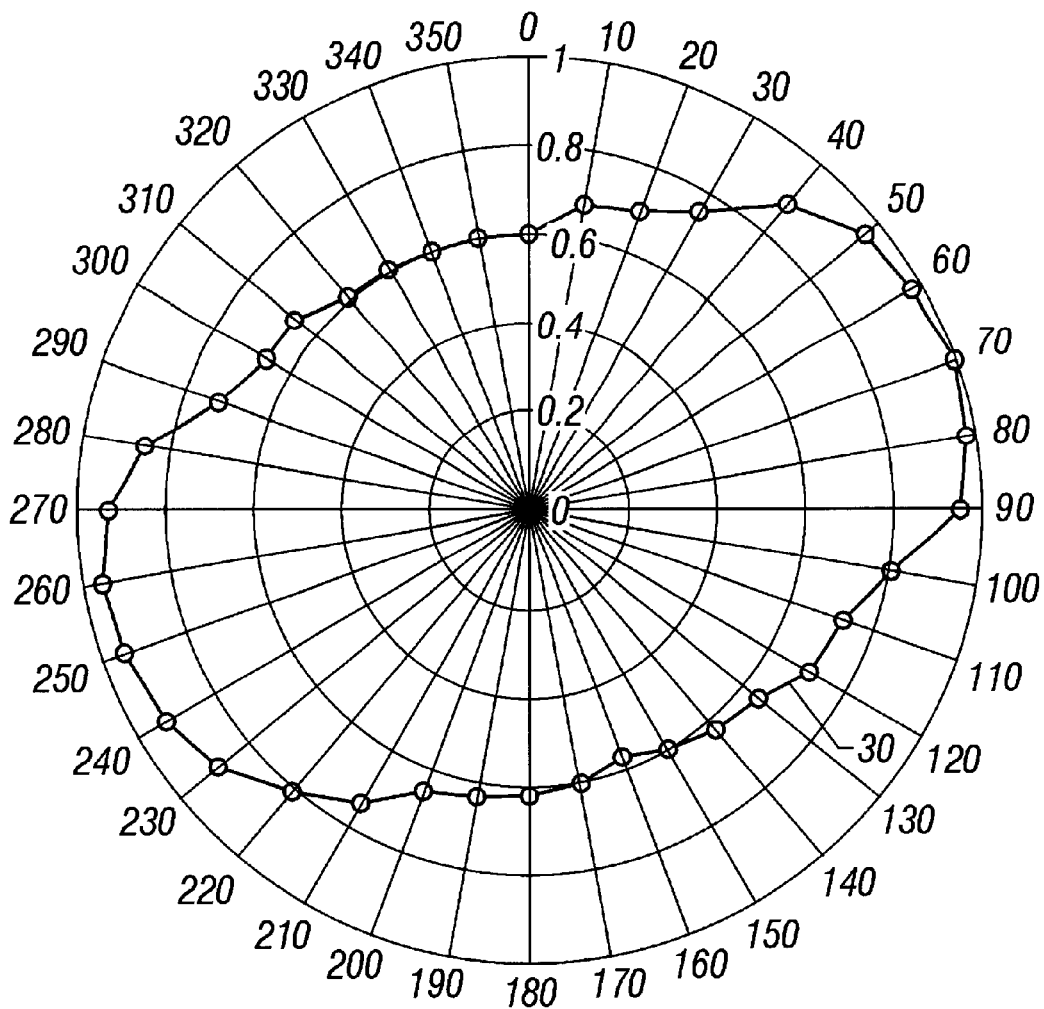
FIG. 8 a polar angle diagram of the intensity distribution of light, which emerges from the skin around an irradiated site. Measured in the abdominal region of the body as shown in FIGS. 6 and 7.
Figure 9:
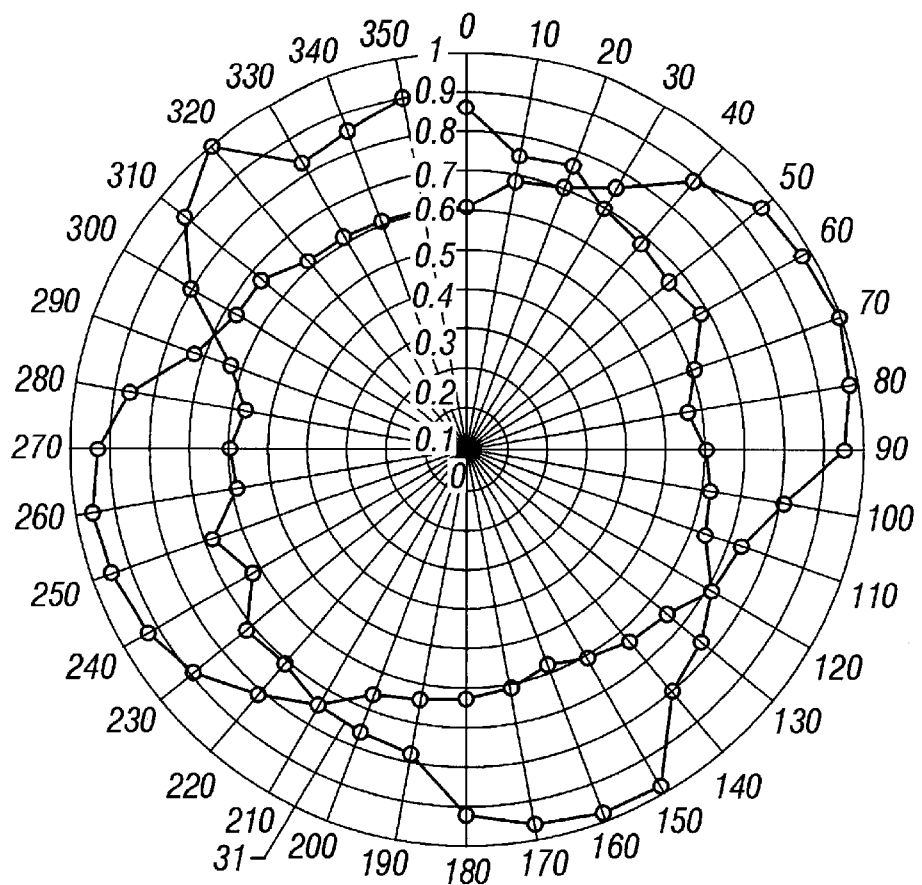
FIG. 9 a polar angle diagram as shown in FIG. 8. Two different measurement distances between irradiation site and detection sites are shown.

A skilled person can easily determine the polar angle dependence of the intensity of secondary light emitted from the skin [5] using an apparatus as shown in FIGS. 1 to 4. It is generally advantageous, as already discussed, to use those measurement signals of the detectors [17] for a given polar angle dependence, whose corresponding light transmission area [21], respectively detection sites [15] are in equal distance to the irradiated site [7], hence, a circle around the light transmission area [9] of the primary light. Two such circles with measurement distances D1 and D2 are shown in FIG. 4 as dashed lines. The polar dependence of the light intensity can be directly derived from the measured intensities and displayed in a suitable way, e.g. as a polar diagram (as shown in FIGS. 8 and 9).

The use of a two dimensional detector array (as shown in FIG. 4) offers the advantage, that a large number of data can be acquired about the distribution of the secondary light near the irradiated site. Thus it is possible to determine the polar dependence of the intensity for different measurement distances between irradiated site and detection site. Besides, modern methods of image processing can be used to determine the preferential direction of light transport. It may be suitable to determine the polar angle dependence for a variety of measurement distances and then to derive the preferential direction globally, e.g. by averaging the distances or the application of a specific algorithm.

Figure 1:
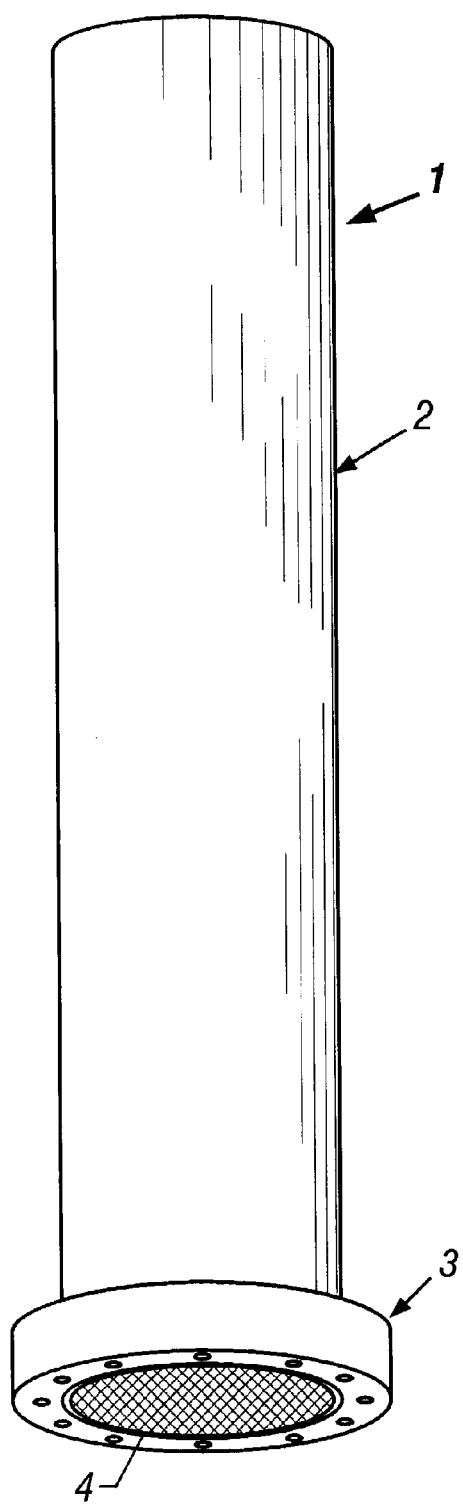
FIG. 1 shows an apparatus for the detection of the direction of Langer's lines in a perspective view from one side.
Figure 2:
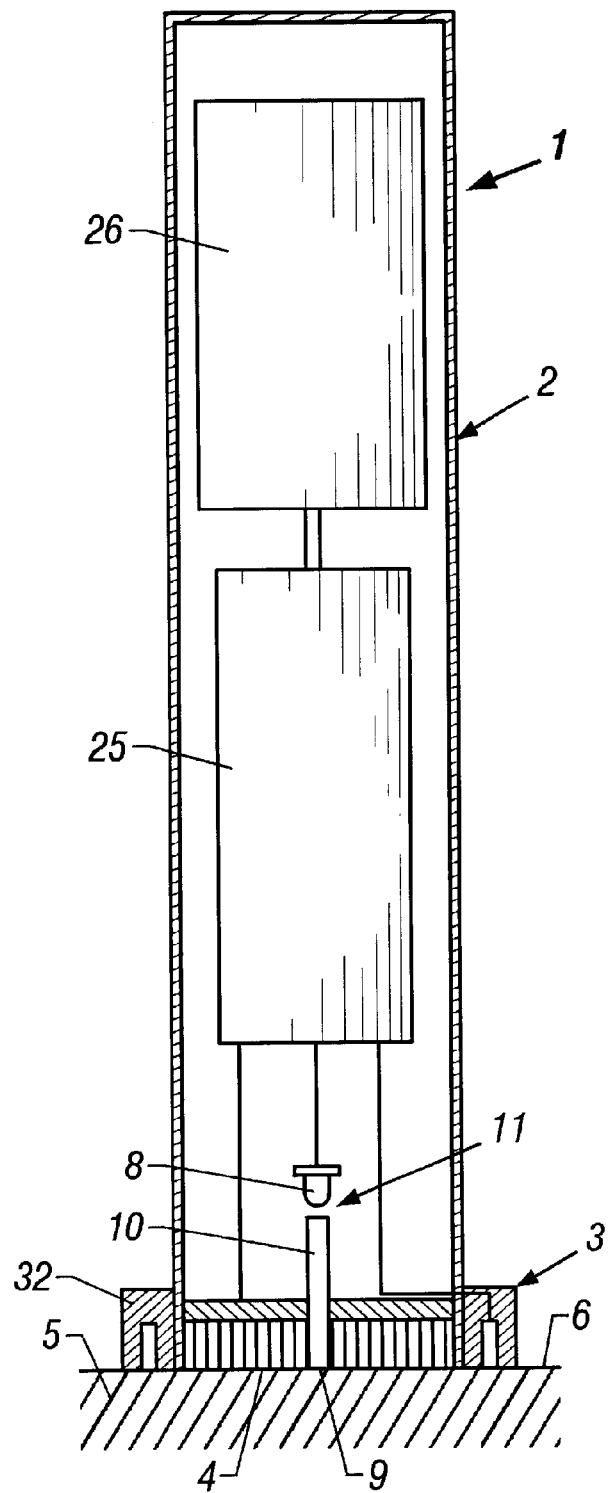
FIG. 2 shows a cut through the apparatus according to FIG. 1, in which the electronic circuits are shown as a block diagram.
Figure 3:
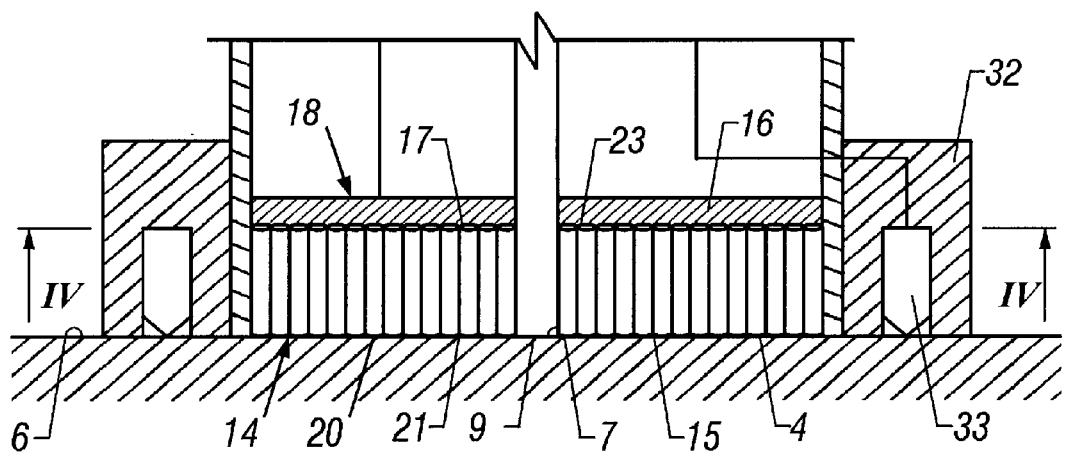
FIG. 3 shows a detailed view of a portion of the apparatus in FIG. 2, which is in direct contact with the skin.
Figure 5:
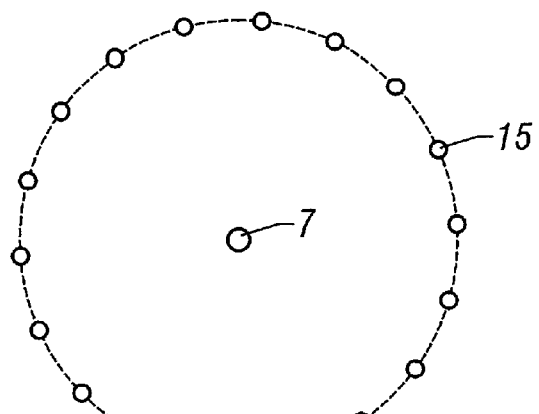
FIG. 5 the alignment of irradiation site and detection sites in an alternative embodiment of a light detection unit.

In principle, the polar dependence at a single distance is sufficient to determine the preferential direction of light transport. Therefore, a simple apparatus can be used successfully for the invention, in which a relatively small number of detection sites [15] is employed, which are aligned on a circle around the irradiated site [7]. Such an alignment is shown in FIG. 5. This can be achieved easily, e.g. by replacement of the CCD array, as shown in FIGS. 1 to 3, by a set of single detectors (e.g. photo diodes, especially avalanche photo diodes) in a circular alignment. In this case, single light guide cylinders or optical fibers can be used instead of the fiber plate [20]. It is also possible to place the detectors in close proximity to the skin surface at the respective detection sites. To ensure a good special resolution of the determination of the polar angle dependence, at least nine detection sites [15] should be located at different polar angles around the irradiated site [7].

Figure 6:
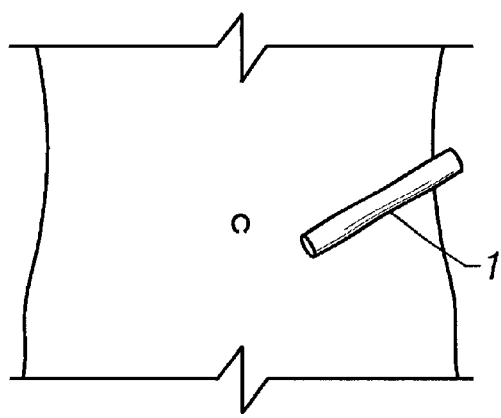
FIG. 6 a drawing of the principle to explain the use of an apparatus, according to the invention in abdominal region of the body.
Figure 7:
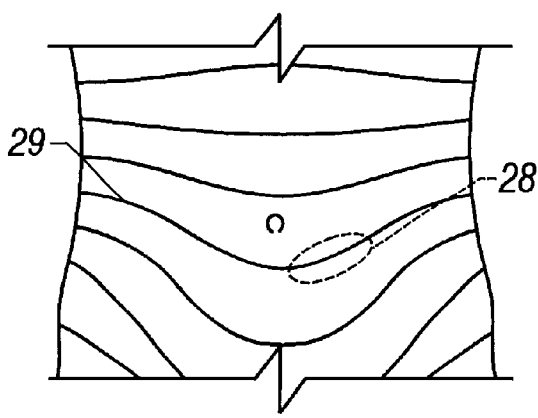
FIG. 7 the usual direction and pattern of Langers lines in the same abdominal region as shown in FIG. 6.

FIGS. 6 and 7 symbolically show the positioning of an apparatus [1] according to the invention in a region [28] of the human body, in which the Langer lines [29] exhibit the indicated pattern. FIG. 8 shows a corresponding polar plot for a light wavelength of 800 nm and a measurement distance of 6 mm. The intensity was normalized to the maximum intensity and is shown in arbitrary units of the scale along the zero degree trajectory. The preferential direction is clearly visible: The light intensity at 70 degrees and in the corresponding opposite direction (250 degrees) is nearly twice as high as the minimal intensity (at about 160 degrees and 340 degrees). The comparison with the Langer's lines in this region of the skin shows that the light intensity is a reliable indicator of the direction of Langer's lines.

Two different polar angle plots are shown in FIG. 9, namely the same intensity distribution shown in FIG. 8 obtained at a measurement distance of 6 mm and a second intensity distribution [31] for a measurement distance of 0.67 mm. All other measurement conditions (apart from the distance) were the same. The intensity distribution [31] shows a different dependence of the intensity on the polar angle with a preferential direction which is orthogonal to the preferential direction shown by the intensity distribution [30]. According to the current knowledge of the inventors, this can be explained by the alignment of the collagen fibers in the upper layers of the skin, which are responsible for the intensity distribution at short distances. The alignment of the upper collagen fibers is orthogonal to those in deeper skin layers. This finding is a further indication of the precision of the invention and the possibility to determine the direction of collagen fiber alignment in different skin depths by using different measurement distances. However, for the determination of the relevant direction of the Langer's lines for surgical cuts, it is preferred that at least some of the measurements for the determination of the direction of light transport are carried out at measurement distances of at least 2 mm. A practical maximum measurement distance is approximately 20 mm. In other words, the area of the skin surface in which the polar dependence of the secondary light emitted by the skin around the irradiated site [7] is determined, should include distances from the irradiated site of less than 20 mm.

As part of the invention, the preferential direction of the light intensity and therefore the direction of the Langer's lines is displayed by means of suitable display means, such that (e.g. as part of a surgical operation) the information about the direction of the Langer's lines is available in a reliable and straight forward manner at any required location of the skin surface. Two fundamentally different methods may be used for this.

The display means can include a marking unit [32], which is directly attached to the apparatus [1]. According to the embodiment as shown in FIGS. 1 to 4, a circular array of printing elements [33] is shown which are controlled by the electronic unit [25] and which generate a marking on the skin that corresponds to the preferhential direction by means of a printing principle (e.g. ink jet). The printing step may be initiated by the user at the required location. The printed marks show the direction of the preferential direction of light transport and therefore the Langer's lines.

For many applications the display of Langer's lines using a printing unit directly attached to the apparatus [1] may not be sufficient. Often, the information is required for a larger skin area. Therefore, the apparatus [1] has to be drawn over the skin and the display of the Langer's lines needs to be done on a larger skin area or on an image of the skin surface.

Figure 10:
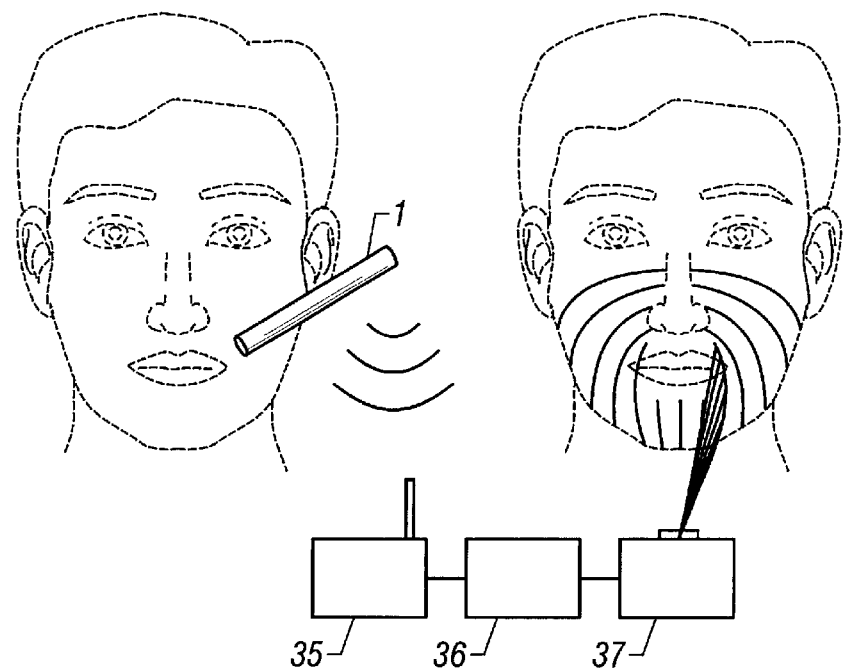
FIG. 10 a drawing of the principle of an alternative embodiment with the display of Langer's lines directions on the skin surface using laser projection.

The important elements of such an embodiment is schematically shown in FIG. 10. The respective position of apparatus [1] is determined wirelessly by a position detector and transmitted to a computer [36]. The position detector [35] and the computer [36] together form a computer controlled positioning system. Such systems are e.g. used during brain surgery and allow a very high accuracy in the determination of a position of an object, such as apparatus [1] in this application.

The information about the respective direction of the Langer's lines is simultaneously transmitted with the information about the position of apparatus [1] from apparatus [1] to computer [36]. The computer calculates the direction of the Langer 's lines, which is then made visible on the skin surface using suitable display means, such as a laser projector [37], as shown in FIG. 10. Alternatively, it is possible (e.g. through laser scanning) to generate a three dimensional image of the skin surface of a patient in a computer and to display the Langer's lines on the computer screen, together with an image of the skin surface, in such a way that the surgeon or other user can recognize the direction of Langer's lines in any required region of the patient's skin.

We claim:

1. A method for the detection of the optimal direction of a surgical cut in skin in-vivo comprising the steps of:
   irradiating light into the skin at a point size irradiation site;
   scattering and absorbing the light within the skin;
   measuring the polar angle dependence of a portion of the irradiated light as it emerges near the irradiated site;
   determining a preferential direction of diffuse light transport within the skin and;
   deriving the direction of the optimal surgical cut line from the determined preferential direction of the light transport.

2. Method according to claim 1, wherein the diameter of the irradiation site is smaller than 1 mm.

3. Method according to claim 1, wherein the polar angle dependence is determined by a measurement of a measurable property of light on at least two measurement locations, which have a polar angle distance of more than 35°.

4. Method according to claim 3, wherein the polar angle dependence is determined by a measurement of a measurable property of light on at least three measurement locations, which have a polar angle distance of equal or less than 20°.

5. Method according to claim 3, wherein the measurable property is the intensity of the light used for irradiation of the skin.

6. Method according to claim 1, wherein several detection sites are aligned at different distances to the irradiated site.

7. Method according to claim 1, wherein the area, in which the polar angle dependence of the emerging light from the skin around the irradiated site is measured, includes distances from the irradiated site of less than 20 mm.

8. Method according to claim 1, wherein the measurable quantity of the light used for irradiation of the skin is between 400 nm and 1400 nm.

9. Method according to claim 1, wherein the wavelength of the primary light is between 400 nm and 1400 nm.

10. Method according to claim 1, wherein the half-width full-maximum wavelength of the light used for irradiation of the skin is less than 200 nm.

11. Method according to claim 1, wherein the light used for irradiation of the skin is polarized.

12. Method according to claim 1, wherein the polarization of the light emerging from the skin is analyzed with a polarization filter, which is located within the light path of the light emerging from the skin.

13. An apparatus comprising:
   measurement means with illumination means to provide light to a skin surface at an irradiation location;
   detection means to measure the polar dependence of a measurable property of the light emerging from the skin near the irradiation location;
   computing means to determine the preferential direction of the light transport in the skin based on the polar dependence of the measurable property of the light emerging from the skin and,
   display means to display the direction of an optimal surgical cut line on the skin surface.

14. Apparatus according to claim 13 comprising an optical fiber plate, wherein one side of the fiber plate forms a contact surface for contact with the skin and the detection means are located on the opposite surface of the fiber plate.

15. Apparatus according to claims 13, wherein the detection means include a CCD array.

16. An apparatus comprising:
   measurement means with illumination means to provide a primary light to a skin surface at on irradiation location;
   detection means to measure the polar dependence of a measurable property of the secondary light emerging from the skin near the irradiation location;
   computing means to determine the preferential direction of the light transport and,
   display means to display the direction of an optimal surgical cut line on the skin surface,
   wherein the detection means include a CCD array, and wherein the display means comprises marking means, directly attached to the measurement means, to generate a mark on the skin surface, which shows the direction of the optimal surgical cut line.

17. Apparatus according to claim 16, wherein the display means comprise a computer controlled position detection system, to determine the current position of the measurement means, and the display means generate an image of the optimal surgical cut line on the skin or on a computer image of the skin surface.

* * * * *